United States Patent
Mockel et al.

(10) Patent No.: US 7,205,144 B2
(45) Date of Patent: Apr. 17, 2007

(54) **NUCLEOTIDE SEQUENCES ENCODING A SENSOR KINASE, CITA, FROM *CORYNEBACTERIUM GLUTAMICUM***

(75) Inventors: Bettina Mockel, Dusseldorf (DE); Mike Farwick, Bielefeld (DE); Thomas Hermann, Bielefeld (DE); Achim Marx, Bielefeld (DE); Walter Pfefferle, Halle (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 10/977,474

(22) Filed: Nov. 1, 2004

(65) Prior Publication Data

US 2005/0112664 A1    May 26, 2005

Related U.S. Application Data

(62) Division of application No. 09/804,060, filed on Mar. 13, 2001, now Pat. No. 6,825,030.

(30) Foreign Application Priority Data

Aug. 31, 2000  (DE) ................. 100 42 740
Feb. 22, 2001  (DE) ................. 101 08 463

(51) Int. Cl.
```
C12N 15/00     (2006.01)
C12N 1/20      (2006.01)
C12N 5/00      (2006.01)
C07H 21/02     (2006.01)
C07H 21/04     (2006.01)
C12N 9/12      (2006.01)
C12P 21/06     (2006.01)
C12Q 1/48      (2006.01)
C07K 1/00      (2006.01)
```
(52) U.S. Cl. ................ 435/252.3; 435/320.1; 435/69.1; 435/325; 435/194; 435/252.33; 435/252.32; 435/15; 536/23.1; 536/23.2; 530/350

(58) Field of Classification Search ............. 435/194, 435/320.1, 69.1, 325, 252.3, 252.32, 252.33, 435/15; 530/350; 536/23.1, 23.2
See application file for complete search history.

(56) References Cited

U.S. PATENT DOCUMENTS 6,825,030 B2 * 11/2004 Mockel et al. ......... 435/252.33
6,831,165 B1 * 12/2004 Pompejus et al. ......... 536/23.1
2002/0086372 A1 * 7/2002 Mockel et al. ............ 435/115
2002/0197605 A1 * 12/2002 Nakagawa et al. ............ 435/6

FOREIGN PATENT DOCUMENTS

| EP | 1 094 111 | | 4/2001 |
| EP | 1 096 013 | | 5/2001 |
| EP | 1 106 693 | | 6/2001 |
| EP | 1 108 790 A2 | | 6/2001 |
| EP | 1108790 | * | 6/2001 |
| WO | WO 01/00842 | | 1/2001 |
| WO | WO200100842 | * | 1/2001 |
| WO | WO2003040181 | * | 5/2003 |

OTHER PUBLICATIONS

Witkowski et al., Biochemistry 38:11643-11650, 1999.*
Seffernick et al., J. Bacteriol. 183(8):2405-2410, 2001.*
Branden et al., Introduction to Protein Structure, Garland Publishing Inc., New York, p. 247, 1991.*
Irwin et al., J. Biol. Chem. 265(9):4944-4952, 1990.*
Sambrook et al., Molecular Cloning, CSHL Press, vol. 1, pp. 4.12-4.13, 4.35, 1989.*
Irwin et al., PIR accession No. H35558, 1990.*
Database EMBL: Accession No. AL022374; Apr. 1998.
Kramer, "Genetic and physiological approaches for the production of amino acids," *Journal of Biotechnology*, vol. 45, No. 1, pp. 1-21.
Elkmanns et al., "Molecular aspects of lysine, threonine, and isoleucine biosynthesis in *Corynebacterium glutamicum*," *Antonie Van Leeuwenhoek*, vol. 64, No. 2, pp. 145-163.
Reinelt et al., The Structure of the Periplasmic Ligand-Binding Domain of the Sensor Kinase CitA Reveals the First Extracellular PAS Domain, J. Biol. Chem. 278(40); 39189-39196 (2003).
Gerharz et al., Identification of Basic Amino Acid Residues Important for Citrate Binding by the Periplasmic Receptor Domain of the Sensor Kinase CitA, Biochemistry, 42:5917-5924 (2003).
GenBank Accession No. AP005274 Created Jun. 5, 2002.
GenBank Accession No. U314464, Jan. 7, 1997.
Mizuki et al., GenBank Accession No. D84354 Published Sep. 11, 1997.

* cited by examiner

*Primary Examiner*—Rebecca E. Prouty
*Assistant Examiner*—Delia M. Ramirez
(74) *Attorney, Agent, or Firm*—Pillsbury Winthrop Shaw Pittman LLP (57) ABSTRACT

The invention related to an isolated nucleic acid consisting of a fragment of the polynucleotide of *Corynebacterium glutamicum* citA gene or a fragment of the full complement of the polynucleotide of the *C. glutamicum* citA gene wherein said fragment is at least 30 consecutive nucleotide in length, and the vector and host cell harboring these nucleic acids.

4 Claims, 1 Drawing Sheet

Figure 1: Plasmid pCR2.1citAint

SEQUENCE LISTING

<160> NUMBER OF SEQ ID NOS: 5

<210> SEQ ID NO 1
<211> LENGTH: 2055
<212> TYPE: DNA
<213> ORGANISM: Corynebacterium glutamicum
<220> FEATURE:
<221> NAME/KEY: CDS
<222> LOCATION: (201)..(1853)
<223> OTHER INFORMATION: citA-Gen

<400> SEQUENCE: 1

```
tttctgtgtt tctcgaaact ttgagatccc gagtgttctg tgttgcttgt gggagtataa      60
ggtggcgcgt gtcacgcaca gaagtgtttg gtgcattgcc tgaggtagtg cgcaaaataa     120
gacttttgtg cattatgatc agaattgttg gcctgggact tcgcttcacg ctctgctgat     180
aatcgccccc gggggtagac atg tct gtt ggt gga tcc gac tgg aaa aac ttc    233
                      Met Ser Val Gly Gly Ser Asp Trp Lys Asn Phe
                       1               5                  10 aag gag gtg gac atc att cgc ttt gct acc cga ata ctg gtg att caa      281
Lys Glu Val Asp Ile Ile Arg Phe Ala Thr Arg Ile Leu Val Ile Gln
             15                  20                  25 gtg gct acc gtc gcg ttg gtg gta gct att tgc acc gga att ttc gca      329
Val Ala Thr Val Ala Leu Val Val Ala Ile Cys Thr Gly Ile Phe Ala
         30                  35                  40 gtt ttg atg atg gat cag atg aaa act gag gcc gag cac aca gcg ctg      377
Val Leu Met Met Asp Gln Met Lys Thr Glu Ala Glu His Thr Ala Leu
     45                  50                  55 tcc atc gga cgt tcg gtg gca tcc aac ccg cag atc cgc gag gaa gta      425
Ser Ile Gly Arg Ser Val Ala Ser Asn Pro Gln Ile Arg Glu Glu Val
 60                  65                  70                  75 gcg ctt gat act caa aca gga gca aac cca tcg gcc gaa gaa tta gcc      473
Ala Leu Asp Thr Gln Thr Gly Ala Asn Pro Ser Ala Glu Glu Leu Ala
                 80                  85                  90 gat gga gat atc caa gcg gtt gca cag gcg gcc aat gaa cgc act gga      521
Asp Gly Asp Ile Gln Ala Val Ala Gln Ala Ala Asn Glu Arg Thr Gly
             95                 100                 105 gct ttg ttt gtc gtt atc act gac ggt tta ggt atc cgc ctg tcc cac      569
Ala Leu Phe Val Val Ile Thr Asp Gly Leu Gly Ile Arg Leu Ser His
        110                 115                 120 cca gat gag gaa cgt ctg ggg gag cag gtg agc act agc ttt gag gct      617
Pro Asp Glu Glu Arg Leu Gly Glu Gln Val Ser Thr Ser Phe Glu Ala
    125                 130                 135 gcc atg cgg ggt gaa gaa acc atg gcg tgg gag act ggg acc ctc ggt      665
Ala Met Arg Gly Glu Glu Thr Met Ala Trp Glu Thr Gly Thr Leu Gly
140                 145                 150                 155 gcg tcc gcg cga gca aaa gtg cct atc ttt gcg ccg gat tct agt gtt      713
Ala Ser Ala Arg Ala Lys Val Pro Ile Phe Ala Pro Asp Ser Ser Val
                160                 165                 170 cca gtc ggt gag gtc agt gtt ggg ttt gag cga gac agt gtg tat tcc      761
Pro Val Gly Glu Val Ser Val Gly Phe Glu Arg Asp Ser Val Tyr Ser
            175                 180                 185 cgc ctg ccc atg ttc ctc gcc gcc ctt gct ctt att tct gtg ttg gga      809
Arg Leu Pro Met Phe Leu Ala Ala Leu Ala Leu Ile Ser Val Leu Gly
        190                 195                 200 atc ctt atc ggc gtg ggt gta gcc atg ggc atg cga cgc cgt tgg gaa      857
Ile Leu Ile Gly Val Gly Val Ala Met Gly Met Arg Arg Arg Trp Glu
    205                 210                 215
```

-continued

| | |
|---|---|
| cgc gtg acc ttg ggt ttg cag ccg gag gag cta gtg acc ctt gtg caa<br>Arg Val Thr Leu Gly Leu Gln Pro Glu Glu Leu Val Thr Leu Val Gln<br>220                       225                       230                       235 | 905 |
| aat cag act gca gtc atc gat ggc att gat gag ggc gtg ctg gcg ctg<br>Asn Gln Thr Ala Val Ile Asp Gly Ile Asp Glu Gly Val Leu Ala Leu<br>                     240                       245                       250 | 953 |
| agc cca aac gga aca att ggg gtg cat aat gag cag gcg caa tcc atg<br>Ser Pro Asn Gly Thr Ile Gly Val His Asn Glu Gln Ala Gln Ser Met<br>                255                       260                       265 | 1001 |
| att ggt gca ggt cct atg agt ggc agg acg ttg aaa gaa cta ggg ctt<br>Ile Gly Ala Gly Pro Met Ser Gly Arg Thr Leu Lys Glu Leu Gly Leu<br>270                       275                       280 | 1049 |
| gac ctg ggt ctt gat ggc gtt gta ttg cat ggt cag cat ccg gaa acc<br>Asp Leu Gly Leu Asp Gly Val Val Leu His Gly Gln His Pro Glu Thr<br>     285                       290                       295 | 1097 |
| gtt gcc cat aac ggc agg atc ctc tat ctg gat ttc cac ccc gtg cgc<br>Val Ala His Asn Gly Arg Ile Leu Tyr Leu Asp Phe His Pro Val Arg<br>300                       305                       310                       315 | 1145 |
| cgt ggg gat caa gat tta ggc tac gtg gta acc atc cgc gat cgt acc<br>Arg Gly Asp Gln Asp Leu Gly Tyr Val Val Thr Ile Arg Asp Arg Thr<br>                     320                       325                       330 | 1193 |
| gac atc att gaa ctc agt gaa cgc ctc gac tct gtg cgc acc atg acc<br>Asp Ile Ile Glu Leu Ser Glu Arg Leu Asp Ser Val Arg Thr Met Thr<br>                335                       340                       345 | 1241 |
| cac gca ctc cgc gcc cag cgc cac gag ttt gcc aac cgc atc cac acc<br>His Ala Leu Arg Ala Gln Arg His Glu Phe Ala Asn Arg Ile His Thr<br>350                       355                       360 | 1289 |
| gca aca ggg ctt atc gac gcc ggc cgc gtc cac gac gcg gca gag ttt<br>Ala Thr Gly Leu Ile Asp Ala Gly Arg Val His Asp Ala Ala Glu Phe<br>     365                       370                       375 | 1337 |
| cta ggc gat ata tcc cgc aac ggg gga cag tca cat cca ttg atc gga<br>Leu Gly Asp Ile Ser Arg Asn Gly Gly Gln Ser His Pro Leu Ile Gly<br>380                       385                       390                       395 | 1385 |
| tca gcg cac ctc aat gaa gca ttt ttg agc tca ttt tta agt act gct<br>Ser Ala His Leu Asn Glu Ala Phe Leu Ser Ser Phe Leu Ser Thr Ala<br>                400                       405                       410 | 1433 |
| tct att tcg gca tct gaa aag ggc gtt agt ctg cgc atc aac tct gac<br>Ser Ile Ser Ala Ser Glu Lys Gly Val Ser Leu Arg Ile Asn Ser Asp<br>                     415                       420                       425 | 1481 |
| acg ctc atc ctt ggc act gtt aaa gat cca gaa gat gta gca acc att<br>Thr Leu Ile Leu Gly Thr Val Lys Asp Pro Glu Asp Val Ala Thr Ile<br>          430                       435                       440 | 1529 |
| ttg ggt aat tta atc aac aat gcc atc gac gcc gcg gtg gca ggt gaa<br>Leu Gly Asn Leu Ile Asn Asn Ala Ile Asp Ala Ala Val Ala Gly Glu<br>445                       450                       455 | 1577 |
| gcc cca cgg tgg att gag ctt acg ttg atg gat gat gcc gat acg ctg<br>Ala Pro Arg Trp Ile Glu Leu Thr Leu Met Asp Asp Ala Asp Thr Leu<br>460                       465                       470                       475 | 1625 |
| gtc att tct gtt gca gat tct ggt cct gga atc cca gag ggc gtg gat<br>Val Ile Ser Val Ala Asp Ser Gly Pro Gly Ile Pro Glu Gly Val Asp<br>                     480                       485                       490 | 1673 |
| gta ttt gcc aca gcc acc cag ata gga gac tct gaa gat aat gaa cgc<br>Val Phe Ala Thr Ala Thr Gln Ile Gly Asp Ser Glu Asp Asn Glu Arg<br>               495                       500                       505 | 1721 |
| acc cac ggg cat ggc att ggt cta aaa ctg tgc cgg gct ttg gct aga<br>Thr His Gly His Gly Ile Gly Leu Lys Leu Cys Arg Ala Leu Ala Arg<br>510                       515                       520 | 1769 |
| tca cat ggt ggc gat gtc tgg gtg att gat aga gga acc gaa gat ggc<br>Ser His Gly Gly Asp Val Trp Val Ile Asp Arg Gly Thr Glu Asp Gly<br>     525                       530                       535 | 1817 |

-continued

```
gct gta ttt gga gtg aaa cta ccg gga gta atg gag taatggatca         1863
Ala Val Phe Gly Val Lys Leu Pro Gly Val Met Glu
540                 545                 550 aacacttaaa gttttagtaa ttgatgatga tttccgcgtc gccggcattc acgcctccat   1923
cgttgatgcg tccctggat tttcggtggt cggtaccgcg cgtaccctcg cagaggcaaa    1983
aaccctgatc gccacatttt ccccggatct cctacttgtt gatgtctacc tccccgacgg   2043
cgatggcatt ga                                                       2055

<210> SEQ ID NO 2
<211> LENGTH: 551
<212> TYPE: PRT
<213> ORGANISM: Corynebacterium glutamicum

<400> SEQUENCE: 2

Met Ser Val Gly Gly Ser Asp Trp Lys Asn Phe Lys Glu Val Asp Ile
1               5                   10                  15

Ile Arg Phe Ala Thr Arg Ile Leu Val Ile Gln Val Ala Thr Val Ala
                20                  25                  30

Leu Val Val Ala Ile Cys Thr Gly Ile Phe Ala Val Leu Met Met Asp
            35                  40                  45

Gln Met Lys Thr Glu Ala Glu His Thr Ala Leu Ser Ile Gly Arg Ser
        50                  55                  60

Val Ala Ser Asn Pro Gln Ile Arg Glu Glu Val Ala Leu Asp Thr Gln
65                  70                  75                  80

Thr Gly Ala Asn Pro Ser Ala Glu Glu Leu Ala Asp Gly Asp Ile Gln
                85                  90                  95

Ala Val Ala Gln Ala Ala Asn Glu Arg Thr Gly Ala Leu Phe Val Val
            100                 105                 110

Ile Thr Asp Gly Leu Gly Ile Arg Leu Ser His Pro Asp Glu Glu Arg
        115                 120                 125

Leu Gly Glu Gln Val Ser Thr Ser Phe Glu Ala Ala Met Arg Gly Glu
    130                 135                 140

Glu Thr Met Ala Trp Glu Thr Gly Thr Leu Gly Ala Ser Ala Arg Ala
145                 150                 155                 160

Lys Val Pro Ile Phe Ala Pro Asp Ser Ser Val Pro Val Gly Glu Val
                165                 170                 175

Ser Val Gly Phe Glu Arg Asp Ser Val Tyr Ser Arg Leu Pro Met Phe
            180                 185                 190

Leu Ala Ala Leu Ala Leu Ile Ser Val Leu Gly Ile Leu Ile Gly Val
        195                 200                 205

Gly Val Ala Met Gly Met Arg Arg Arg Trp Glu Arg Val Thr Leu Gly
    210                 215                 220

Leu Gln Pro Glu Glu Leu Val Thr Leu Val Gln Asn Gln Thr Ala Val
225                 230                 235                 240

Ile Asp Gly Ile Asp Glu Gly Val Leu Ala Leu Ser Pro Asn Gly Thr
                245                 250                 255

Ile Gly Val His Asn Glu Gln Ala Gln Ser Met Ile Gly Ala Gly Pro
            260                 265                 270

Met Ser Gly Arg Thr Leu Lys Glu Leu Gly Leu Asp Leu Gly Leu Asp
        275                 280                 285

Gly Val Val Leu His Gly Gln His Pro Glu Thr Val Ala His Asn Gly
    290                 295                 300

Arg Ile Leu Tyr Leu Asp Phe His Pro Val Arg Arg Gly Asp Gln Asp
305                 310                 315                 320
```

```
Leu Gly Tyr Val Val Thr Ile Arg Asp Arg Thr Asp Ile Ile Glu Leu
            325                 330                 335
Ser Glu Arg Leu Asp Ser Val Arg Thr Met Thr His Ala Leu Arg Ala
            340                 345                 350
Gln Arg His Glu Phe Ala Asn Arg Ile His Thr Ala Thr Gly Leu Ile
            355                 360                 365
Asp Ala Gly Arg Val His Asp Ala Ala Glu Phe Leu Gly Asp Ile Ser
            370                 375                 380
Arg Asn Gly Gly Gln Ser His Pro Leu Ile Gly Ser Ala His Leu Asn
385                 390                 395                 400
Glu Ala Phe Leu Ser Ser Phe Leu Ser Thr Ala Ser Ile Ser Ala Ser
                    405                 410                 415
Glu Lys Gly Val Ser Leu Arg Ile Asn Ser Asp Thr Leu Ile Leu Gly
                    420                 425                 430
Thr Val Lys Asp Pro Glu Asp Val Ala Thr Ile Leu Gly Asn Leu Ile
            435                 440                 445
Asn Asn Ala Ile Asp Ala Ala Val Ala Gly Glu Ala Pro Arg Trp Ile
450                 455                 460
Glu Leu Thr Leu Met Asp Asp Ala Asp Thr Leu Val Ile Ser Val Ala
465                 470                 475                 480
Asp Ser Gly Pro Gly Ile Pro Glu Gly Val Asp Val Phe Ala Thr Ala
                    485                 490                 495
Thr Gln Ile Gly Asp Ser Glu Asp Asn Glu Arg Thr His Gly His Gly
            500                 505                 510
Ile Gly Leu Lys Leu Cys Arg Ala Leu Ala Arg Ser His Gly Gly Asp
            515                 520                 525
Val Trp Val Ile Asp Arg Gly Thr Glu Asp Gly Ala Val Phe Gly Val
            530                 535                 540
Lys Leu Pro Gly Val Met Glu
545                 550
```

<210> SEQ ID NO 3
<211> LENGTH: 481
<212> TYPE: DNA
<213> ORGANISM: Corynebacterium glutamicum
<220> FEATURE:
<223> OTHER INFORMATION: citAint

<400> SEQUENCE: 3

```
ttccagtcgg tgaggtcagt gttgggtttg agcgagacag tgtgtattcc cgcctgccca    60
tgttcctcgc cgcccttgct cttatttctg tgttgggaat ccttatcggc gtgggtgtag   120
ccatgggcat cgacgccgt tgggaacgcg tgaccttggg tttgcagccg gaggagctag   180
tgacccttgt gcaaaatcag actgcagtca tcgatggcat tgatgagggc gtgctggcgc   240
tgagcccaaa cggaacaatt ggggtgcata atgagcaggc gcaatccatg attggtgcag   300
gtcctatgag tggcaggacg ttgaaagaac tagggcttga cctgggtctt gatggcgttg   360
tattgcatgg tcagcatccg gaaaccgttg cccataacgg caggatcctc tatctggatt   420
ccaccccgt gcgccgtggg gatcaagatt taggctacgt ggtaaccatc cgcgatcgta   480
c                                                                  481
```

<210> SEQ ID NO 4
<211> LENGTH: 20
<212> TYPE: DNA
<213> ORGANISM: Corynebacterium glutamicum -continued

```
<220> FEATURE:
<223> OTHER INFORMATION: Primer citA-int1

<400> SEQUENCE: 4
ttccagtcgg tgaggtcagt                                          20

<210> SEQ ID NO 5
<211> LENGTH: 20
<212> TYPE: DNA
<213> ORGANISM: Corynebacterium glutamicum
<220> FEATURE:
<223> OTHER INFORMATION: Primer citA-int2

<400> SEQUENCE: 5
gtacgatcgc ggatggttac                                          20
```

NUCLEOTIDE SEQUENCES ENCODING A SENSOR KINASE, CITA, FROM CORYNEBACTERIUM GLUTAMICUM

This is a divisional of U.S. patent application Ser. No. 09/804,060 filed Mar. 13, 2001, now U.S. Pat. No. 6,825,030, which claims priority to German Patent Appl. No. 100 42 740.5, filed Aug. 31, 2000, and German Patent Appl. No. 101 08 463.3 filed Feb. 22, 2001.

The invention provides nucleotide sequences from coryneform bacteria which code for the citA gene and a process for the fermentative preparation of amino acids, in particular L-lysine, by attenuation of the citA gene. The citA gene codes for the sensor kinase Cit A of a two-component system.

BACKGROUND OF THE INVENTION

L-Amino acids, in particular L-lysine, are used in human medicine and in the pharmaceuticals industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce amino acids are obtained in this manner.

Methods of the recombinant DNA technique have also been employed for some years for improving the strain of *Corynebacterium* strains which produce L-amino acids.

OBJECT OF THE INVENTION

The inventors had the object of providing new measures for improved fermentative preparation of amino acids, in particular L-lysine.

BRIEF DESCRIPTION OF THE INVENTION

If L-lysine or lysine are mentioned in the following, this also means the salts, such as e.g. lysine monohydrochloride or lysine sulfate.

The invention provides an isolated polynucleotide from coryneform bacteria, comprising a polynucleotide sequence which codes for the citA gene chosen from the group consisting of
a) polynucleotide which is identical to the extent of at least 70% to a polynucleotide which codes for a polypeptide which comprises the amino acid sequence of SEQ ID No. 2,
b) polynucleotide which codes for a polypeptide which comprises an amino acid sequence which is identical to the extent of at least 70% to the amino acid sequence of SEQ ID No. 2,
c) polynucleotide which is complementary to the polynucleotides of a) or b), and
d) polynucleotide comprising at least 15 successive nucleotides of the polynucleotide sequence of a), b) or c), the polypeptide preferably having the activity of sensor kinase CitA.

The invention also provides the abovementioned polynucleotide, this preferably being a DNA which is capable of replication, comprising:
(i) the nucleotide sequence shown in SEQ ID No.1 or
(ii) at least one sequence which corresponds to sequence (i) within the range of the degeneration of the genetic code, or
(iii) at least one sequence which hybridizes with the sequences complementary to sequences (i) or (ii), and optionally
(iv) sense mutations of neutral function in (i).

The invention also provides:
a polynucleotide, in particular DNA, which is capable of replication and comprises the nucleotide sequence as shown in SEQ ID No.1;
a polynucleotide which codes for a polypeptide which comprises the amino acid sequence as shown in SEQ ID No. 2;
a vector containing parts of the polynucleotide according to the invention, but at least 15 successive nucleotides of the sequence claimed
and coryneform bacteria in which the citA gene is attenuated, in particular by an insertion or deletion.

The invention also provides polynucleotides which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention or a fragment thereof, and isolation of the polynucleotide sequence mentioned.

Polynucleotides comprising the sequences according to the invention are suitable as hybridization probes for RNA, cDNA and DNA, in order to isolate, in the full length, nucleic acids or polynucleotides or genes which code for CitA protein or to isolate those nucleic acids or polynucleotides or genes which have a high similarity with the sequence of the citA gene.

Polynucleotides comprising the sequences according to the invention are furthermore suitable as primers with the aid of which DNA of genes which code for the CitA protein can be prepared by the polymerase chain reaction (PCR).

Such oligonucleotides which serve as probes or primers comprise at least 30, preferably at least 20, very particularly preferably at least 15 successive nucleotides. Oligonucleotides which have a length of at least 40 or 50 nucleotides are also suitable.

DETAILED DESCRIPTION OF THE INVENTION

"Isolated" means separated out of its natural environment.
"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70%, preferably at least 80% and in particular at least 90% to 95% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of the CitA protein and also those which are at least 70%, preferably at least 80% and in particular at least 90% to 95% identical to the polypeptide according to SEQ ID No. 2 and have the activity mentioned.

The invention moreover relates to a process for the fermentative preparation of amino acids, in particular L-lysine, using coryneform bacteria which in particular already produce amino acids and in which the nucleotide sequences which code for the citA gene are attenuated, in particular eliminated or expressed at a low level.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

The microorganisms which the present invention provides can prepare amino acids, in particular L-lysine, from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains
*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 or L-amino acid-producing mutants or strains prepared therefrom, such as, for example, the L-lysine-producing strains
*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464
*Corynebacterium glutamicum* DM58-1
*Corynebacterium glutamicum* DG52-5
*Corynebacterium glutamicum* DSM 5715 and
*Corynebacterium glutamicum* DSM 12866

The inventors have succeeded in isolating the new citA gene of *C. glutamicum* which codes for the CitA protein and which is a sensor kinase of a two-component system.

To isolate the citA gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ-vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575). Börmann et al. (Molecular Microbiology 6(3), 317–326 (1992)) in turn describe a gene library of *C. glutamicum* ATCC13032 using the cosmid pHC79 (Hohn and Collins, 1980, Gene 11, 291–298).

To prepare a gene library of *C. glutamicum* in *E. coli* it is also possible to use plasmids such as pBR322 (Bolivar, 1979, Life Sciences, 25, 807–818) or pUC9 (Vicira et al., 1982, Gene, 19:259–268). Suitable hosts are, in particular, those *E. coli* strains which are restriction- and recombination-defective, such as, for example, the strain DH5α (Jeffrey H. Miller: "A Short Course in Bacterial Genetics, A Laboratory Manual and Handbook for *Escherichia coli* and Related Bacteria", Cold Spring Harbor Laboratory Press, 1992).

The long DNA fragments cloned with the aid of cosmids or other λ-vectors can than be subcloned in turn into the usual vectors suitable for DNA sequencing.

Methods of DNA sequencing are described, inter alia, by Sanger et al. (Proceedings of the National Academy of Sciences of the United States of America USA, 74:5463–5467, 1977).

The resulting DNA sequences can then be investigated with known algorithms or sequence analysis programs, such as e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamicum* which codes for the citA gene and which, as SEQ ID No. 1, is a constituent of the present invention has been found in this way. The amino acid sequence of the corresponding protein has furthermore been derived from the present DNA sequence by the methods described above. The resulting amino acid sequence of the citA gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology 41: 255–260 (1991)). The hybridization takes place under stringent conditions, that is to say only hybrids in which the probe and target sequence, i. e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996). A 5×SSC buffer at a temperature of approx. 50–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approx. 50–68° C. being established. Polynucleotide fragments which are, for example, at least 70% or at least 80% or at least 90% to 95% identical to the sequence of the probe employed can be isolated by increasing the hybridization temperature stepwise from 50 to 68° C. in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: OligonukicotidedesA: a Practical Approach (IRL Press, Oxford, UK, 1984) and in Newton and Graham: PCR (Spektrum Akademischer Verlag, Heidelberg, Germany, 1994).

In the work on the present invention, it has been found that coryneform bacteria produce amino acids, in particular L-lysine, in an improved manner after attenuation of the citA gene.

To achieve an attenuation, either the expression of the citA gene or the catalytic properties of the enzyme protein can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Pátek et al. (Microbiology 142: 1297 (1996)), Vasicova et al. (Journal of Bacteriology 181: 6188 (1999)) and in known textbooks of genetics and molecular biology, such as e.g. the textbook by Knippers ("Molekulare Genetik [Molecular Genetics]", 6th edition, Georg Thieme Verlag, Stuttgart, Germany, 1995) or that by Winnacker ("Gene und Klone [Genes and Clones]", VCH Verlagsgesellschaft, Weinheim, Germany, 1990).

Mutations which lead to a change or reduction in the catalytic properties of enzyme proteins are known from the prior art; examples which may be mentioned are the works by Qiu and Goodman (Journal of Biological Chemistry 272: 8611–8617(1997)), Sugimoto et al. (Bioscience Biotechnology and Biochemistry 61: 1760–1762 (1997)) and Möckel ("Die Threonindehydratase aus *Corynebacterium glutamicum*: Aufhebung der allosterischen Regulation und Struktur des Enzyms [Threonine dehydratase from *Corynebacterium glutamicum*: Cancelling the allosteric regulation and structure of the enzyme]", Reports from the Jülich Research Centre, Jül-2906, ISSN09442952, Jülich, Germany, 1994). Summarizing descriptions can be found in known textbooks of genetics and molecular biology, such as e.g. that by Hagemann ("Allgemeine Genetik [General Genetics]", Gustav Fischer Verlag, Stuttgart, 1986).

Possible mutations are transitions, transversions, insertions and deletions. Depending on the effect of the amino acid exchange on the enzyme activity, missense mutations or nonsense mutations are referred to. Insertions or deletions of at least one base pair (bp) in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik [Molecular Genetics]", 6th edition, Georg Thieme Verlag, Stuttgart, Germany, 1995), that by Winnacker ("Gene und Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986).

A common method of mutating genes of *C. glutamicum* is the method of gene disruption and gene replacement described by Schwarzer and Pühler (Bio/Technology 9, 84–87 (1991)).

In the method of gene disruption a central part of the coding region of the gene of interest is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schafer et al., Gene 145, 69–73 (1994)), pK18mobsacB or pK19mobsacB (Jager et al., Journal of Bacteriology 174: 5462–65 (1992)), pGEM-T (PROMEGA® corporation, Madison, Wis., USA), pCR2.1-TOPO (Shuman (1994). Journal of Biological Chemistry 269:32678–84; U.S. Pat. No. 5,487,993), pCR® BLUNT (INVITROGEN®, Groningen, Holland; Bernard et al., Journal of Molecular Biology, 234: 534–541 (1993)) or pEM1 (Schrumpf et al, 1991, Journal of Bacteriology 173:4510–4516). The plasmid vector which contains the central part of the coding region of the gene is then transferred into the desired strain of *C. glutamicum* by conjugation or transformation. The method of conjugation is described, for example, by Schafer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross-over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575–580 (1994)) to eliminate the recA gene of C. glutamicum.

In the method of gene replacement, a mutation, such as e.g. a deletion, insertion or base exchange, is established in vitro in the gene of interest. The allele prepared is in turn cloned in a vector which is not replicative for C. glutamicum and this is then transferred into the desired host of C. glutamicum by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch et al. (Microbiology 144, 915–927 (1998)) to eliminate the pyc gene of C. glutamicum by a deletion.

A deletion, insertion or a base exchange can be incorporated into the citA gene in this manner.

In addition, it may be advantageous for the production of L-amino acids, in particular L-lysine, to enhance, in particular to over-express, one or more enzymes of the particular biosynthesis pathway, of glycolysis, of anaplerosis, of the pentose phosphate cycle or of amino acid export and optionally regulatory proteins, in addition to attenuation of the citA gene.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

Thus, for example, for the preparation of L-lysine, at the same time one or more of the genes chosen from the group consisting of the dapA gene which codes for dihydrodipicolinate synthase (EP-B 0 197 335), the gap gene which codes for glyceraldehyde 3-phosphate dehydrogenase (Eikmanns (1992), Journal of Bacteriology 174:6076–6086), the zwf gene which codes for glucose 6-phosphate dehydrogenase (JP-A-09224661), the pyc gene which codes for pyruvate carboxylase (DE-A-198 31 609), the lysE gene which codes for lysine export (DE-A-195 48 222)

the lysC gene which codes for a feed back resistant aspartate kinase (EP-B-0387527; EP-A-0699759; WO 00/63388), or the zwa1 gene which codes for the Zwa1 protein (DE: 199 59 328.0, DSM 13115)

can be enhanced, in particular over-expressed.

It may furthermore be advantageous for the production of amino acids, in particular L-lysine, in addition to the attenuation of the citA gene, at the same time for one or more of the genes chosen from the group consisting of the pck gene which codes for phosphoenol pyruvate carboxykinase (DE 199 50 409.1, DSM 13047), the pgi gene which codes for glucose 6-phosphate isomerase (U.S. Ser. No. 09/396,478, DSM 12969), the poxB gene which codes for pyruvate oxidase (DE: 1995 1975.7, DSM 13114)

the zwa2 gene which codes for the Zwa2 protein (DE: 199 59,327.2, DSM 13113)

to be attenuated.

In addition to attenuation of the citA gene it may furthermore be advantageous, for the production of amino acids, in particular L-lysine, to eliminate undesirable side reactions, (Nakayama: "Breeding of Amino Acid Producing Microorganisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids, in particular L-lysine. A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) by anion exchange chromatography with subsequent ninhydrin derivatization, or it can be carried out by reversed phase HPLC, for example as described by Lindroth et al. (Analytical Chemistry (1979) 51: 1167–1174).

The invention furthermore relates to a process for the fermentative preparation of an amino acid chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine, in particular L-lysine, using coryneform bacteria which in particular already produce one or more of the amino acids mentioned.

The following microorganism was deposited on 23.01.2001 as a pure culture at the Deutsche Sammlung für Mikrorganismen und Zellkulturen (DSMZ=German Collection of Microorganisms and Cell Cultures, Braunschweig, Germany) in accordance with the Budapest Treaty:

Escherichia coli strain Top10/pCR2.1citAint as DSM 13998.

The present invention is explained in more detail in the following with the aid of embodiment examples.

The isolation of plasmid DNA from *Escherichia coli* and all techniques of restriction, Klenow, and alkaline phosphatase treatment were carried out by the method of Sambrook et al. (Molecular Cloning. A Laboratory Manual, 1989, Cold Spring Harbor Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

EXAMPLES

Example 1

Preparation of a Genomic Cosmid Gene Library from *C. glutamicum* ATCC 13032

Chromosomal DNA from *C. glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987), Proceedings of the National Academy of Sciences, USA 84:2160–2164), obtained from Stratagene (La Jolla, USA, Product Description SuperCos1 Cosmid Vektor Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamH1 (Amersham, Pharmacia, Freiburg, Germany, Product Description BamH1, Code no 27-0868-04). The cosmid DNA treated in this manner was mixed with the treated ATCC 13032 DNA and the batch was treated wit T4 DNA ligase (Amersham Pharmacia, Freiburg, Germany, Product Description T4-DNA-Ligase, Code no. 27-0870-04). The litigation mixture was then packed in phages with the aid of Gigapack II XL Packing Extract (STRATAGENE®, La Jolla, USA, Product Description Gigapack II XL Packing Extract, Code no. 200217).

For infection of the *E. coli* strain NM554 (Raleigh et al. 1988, Nucleic Acid Res. 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A Laboratory Manual, Cold Spring Harbor), the cells being plated out on LB agar (Lennox, 1955, Virology, 1:190)+100 µg/ml ampicillin. After incubation overnight at 37° C., recombinant individual clones were selected.

Example 2

Isolation and Sequencing of the citA Gene

The cosmid DNA of an individual colony was isolated with the Qiaprep Spin Miniprep Kit (QIAPREP®) (Product No. 27106, QIAGEN®, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII (QIAEX®) Gel Extraction Kit (Product No. 20021, Qiagen, QIAGEN®, Hilden, Germany).

The DNA of the sequencing vector pZero-1 (PZERO®), obtained from Invitrogen® (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 (PZERO®). was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the *E. coli* strain DH5.alpha.MCR (Grant, 1990, Proceedings of the National Academy of Sciences, U.S.A., 87:4645–4649) and plated out on LB agar (Lennox, 1955, Virology, 1:190) with 50 µg/ml zeocin.

The plasmid preparation of the recombinant clones was carried out with Biorobot (BIOROBOT®) 9600 (Product No. 900200, QIAGEN®, Hilden, Germany). The sequencing was carried out by the dideoxy chain termination method of Sanger et al. (1977, Proceedings of the National Academies of Sciences, U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–23 1) version 97-0. The individual sequences of the pZero1 derivatives were assembled to a continuous contig. The computer-assisted coding region analysis were prepared with the XNIP program (Staden, 1986, Nucleic Acids Research, 14:217–231). Further analyses were carried out with the "BLAST search program" (Altschul et al., 1997, Nucleic Acids Research, 25:3389–3402) against the non-redundant databank of the "National Center for Biotechnology Information" (NCBI, Bethesda, Md., USA).

The resulting nucleotide sequence is shown in SEQ ID No. 1. Analysis of the nucleotide sequence showed an open reading frame of 1653 bp, which was called the citA gene. The citA gene codes for a polypeptide of of [sic] 551 amino acids.

Example 3

Preparation of an Integration Vector for Integration Mutagenesis of the citA Gene From the strain ATCC 13032, chromosomal DNA was isolated by the method of Eikmanns et al. (Microbiology 140: 1817–1828(1994)). On the basis of the sequence of the citA gene known for C. glutamicum from example 2, the following oligonucleotides were chosen for the polymerase chain reaction (see SEQ ID No. 4 and SEQ ID No. 5):

```
citA-int1:
5' TTC CAG TCG GTG AGG TCA GT 3' citA-int2:
5' GTA CGA TCG CGG ATG GTT AC 3'
```

The primers shown were synthesized by MWG Biotech (Ebersberg, Germany) and the PCR reaction was carried out by the standard PCR method of Innis et al. (PCR protocols. A guide to methods and applications, 1990, Academic Press) with the Taq-polymerase from Boehringer Mannheim (Germany, Product Description Taq DNA polymerase, Product No. 1 146 165). With the aid of the polymerase chain reaction, the primers allow amplification of an internal fragment of the citA gene 480 bp in size. The product amplified in this way was tested electrophoretically in a 0.8% agarose gel.

The amplified DNA fragment (see SEQ ID NO: 3) was ligated with the TOPO® TA Cloning Kit from INVITROGEN® Corporation (Carlsbad, Calif., USA: Catalogue Number K4500-01) in the vector pCR2.1-TOPO (Mead et al. (1991) Bio/Technology 9:657–663).

Figure 1:
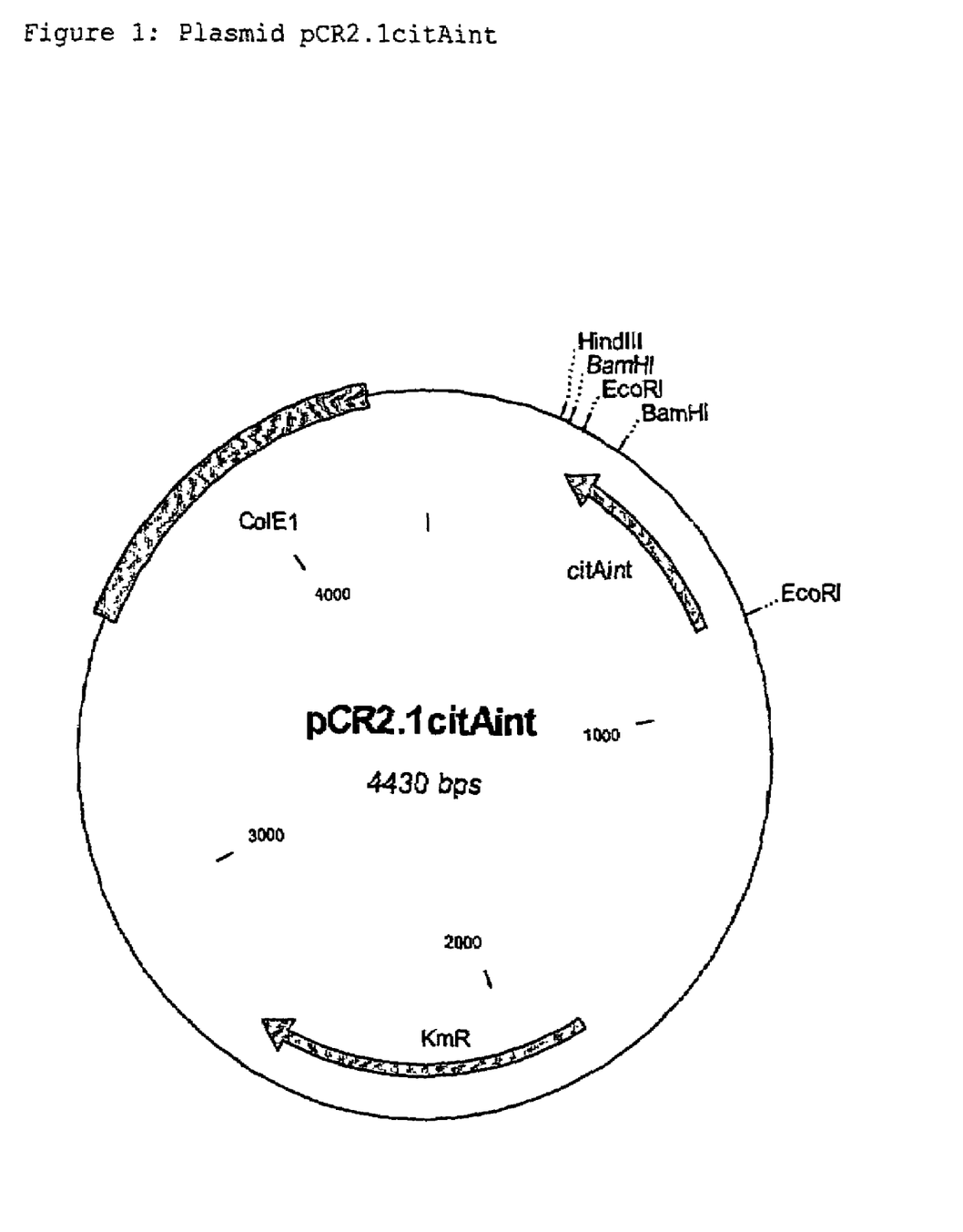
FIG. 1: Plasmid pCR2.1citAint harbors a 480 bp internal fragment of the citA gene and has a kanamycin resistance marker.

The E. coli strain TOP10 was then electroporated with the ligation batch (Hanahan, In: DNA cloning. A practical approach, Vol. I, IRL-Press, Oxford, Washington D.C, USA, 1985). Selection for plasmid-carrying cells was made by plating out the transformation batch on LB agar (Sambrook et al., Molecular cloning: a laboratory manual. $2^{nd}$ Ed. Cold Spring Harbor Laboratory Press, Cold Spring Harbor, N.Y., 1989), which had been supplemented with 50 mg/l kanamycin. Plasmid DNA was isolated from a transformant with the aid of the QIAPREP® Spin Miniprep Kit from QIAGEN® and checked by restriction with the restriction enzyme EcoRI and subsequent agarose gel electrophoresis (0.8%). The plasmid was called pCR2.1citAint and is shown in FIG. 1.

The following microorganism was deposited as a pure culture on Jan. 23, 2001 at the Deutsche Sammlung für Mikroorganismen und Zellkulturen (DSMZ=German Collection of Microorganisms and Cell Cultures, Braunschweig, Germany) in accordance with the Budapest Treaty:

Escherichia coli Top10/pCR2.1citAint as DSM 13998

Example 4

Integration Mutagenesis of the citA Gene in the Strains DSM 5715 and FERM-BP 1763

The vector pCR2.1citAint mentioned in example 3 was electroporated by the electroporation method of Tauch et al. (FEMS Microbiological Letters, 123:343–347 (1994)) into the strains Corynebacterium glutamicum DSM 5715 and Brevibacterium lactofermentum FERM-BP 1763. The strain DSM 5715 is an AEC-resistant lysine producer (EP-B-0435132), and the strain FERM-BP 1763 is a mycophenolic acid-resistant valine producer (U.S. Pat. No. 5,188,948). The vector pCR2.1citAint cannot replicate independently in DSM5715 and FERM-BP 1763 and is retained in the cell only if it has integrated into the chromosome of DSM 5715 or FERM-BP 1763. Selection of clones with pCR2.1citAint integrated into the chromosome was carried out by plating out the electroporation batch on LB agar (Sambrook et al., Molecular cloning: a laboratory manual. $2^{nd}$ Ed. Cold Spring Harbor Laboratory Press, Cold Spring Harbor, N.Y.), which had been supplemented with 15 mg/l kanamycin.

For detection of the integration, the citAint fragment was labelled with the Dig hybridization kit from Boehringer by the method of "The DIG System Users Guide for Filter Hybridization" of Boehringer Mannheim GmbH (Mannheim, Germany, 1993). Chromosomal DNA of in each case a potential integrant was isolated by the method of Eikmanns et al. (Microbiology 140:1817–1828 (1994)) and in each case cleaved with the restriction enzymes EcoRI, BamHI and HindIII. The fragments formed were separated by means of agarose gel electrophoresis and hybridized at 68° C. with the Dig hybridization kit from Boehringer. The plasmid pCR2.1citAint mentioned in example 3 had been inserted into the chromosome of DSM5715 and into the chromosome of FERM-BP 1763 within the chromosomal citA gene. The strains were called DSM5715::pCR2.1citAint and FERM-BP 1763:pCR2.1citAint.

Example 5

Preparation of Lysine

The C. glutamicum strain DSM5715::pCR2.1citAint obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (25 mg/l) for 24 hours at 33° C. Starting from this agar plate culture, a preculture was seeded (10 ml medium in a 100 ml conical flask). The complete medium CgIII was used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH is brought to pH 7.4 | |

Kanamycin (25 mg/l) was added to this. The preculture was incubated for 16 hours at 33° C. at 240 rpm on a shaking machine. A main culture was seeded from this preculture such that the initial OD (660 nm) of the main culture is 0.1 OD. Medium MM was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, and the $CaCO_3$ autoclaved in the dry state was added.

Culturing was carried out in a 10 ml volume in a 100 ml conical flask with baffles. Kanamycin (25 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivatization with ninhydrin detection.

The result of the experiment is shown in table 1.

TABLE 1

| Strain | OD(660) | Lysine HCl g/l |
|---|---|---|
| DSM5715 | 7.5 | 13.3 |
| DSM5715::pCR2.1citAint | 7.4 | 14.4 |

Example 6

Preparation of Valine

The *B. lactofermentum* strain FERM-BP 1763::pCR2.1citAint obtained in example 4 was cultured in a nutrient medium suitable for the production of valine and the valine content in the culture supernatant was determined.

For this, the strain was first incubated on an agar plate with the corresponding antibiotic (brain-heart agar wit kanamycin (25 mg/l) for 24 hours at 33° C. Starting from this agar plate culture, a preculture was seeded (10 ml medium in a 100 ml conical flask). The complete medium CgIII was used as the medium for the preculture. Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1 OD. Medium MM was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Isoleucine (sterile-filtered) | 0.1 g/l |
| Methionine (sterile-filtered) | 0.1 g/l |
| Thiamine * HCl (sterile-filtered) | 0.2 mg/l |
| Leucine (sterile-filtered) | 0.1 g/l |
| $CaCO_3$ | 25 g/l |

The CSL (corn steep liquor), MOPS (morpholinopropanesulfonic acid) and the salt solution were brought to pH 7 with aqueous ammonia and autoclaved. The sterile substrate and vitamin solutions were then added, and the $CaCO_3$ autoclaved in the dry state was added.

Culturing was carried out in a 10 ml volume in a 100 ml conical flask with baffles. Kanamycin (25 mg/l) was added. Culturing was carried out at 33° C. and 80% atmospheric humidity.

After 48 hours, the OD was determined at a measurement wavelength of 660 nm with a Biomek 1000 (Beckmann Instruments GmbH, Munich). The amount of valine formed was determined with an amino acid analyzer from Eppendorf-BioTronik (Hamburg, Germany) by ion exchange chromatography and post-column derivatization with ninhydrin detection.

The result of the experiment is shown in table 2.

TABLE 2

| Strain | OD(660) | Valine HCl g/l |
|---|---|---|
| FERM-BP 1763 | 12.1 | 7.5 |
| FERM-BP 1763::pCR2.1citAint | 13.5 | 10.8 |

The invention claimed is:

1. An isolated nucleic acid consisting of
   (a) a fragment of the polynucleotide of SEQ ID NO: 1; or
   (b) a fragment of the full complement of the polynucleotide of SEQ ID NO: 1, wherein said fragment is at least 30 consecutive nucleotides in length.

2. A vector comprising the nucleic acid of claim 1, wherein said nucleic acid encodes a polypeptide consisting of a fragment of the polypeptide of SEQ ID NO: 2.

3. The vector of claim 2, wherein the vector cannot replicate in *C. glutamicum*.

4. A host cell comprising the vector of claim 2.

* * * * *